(12) United States Patent
Bhardwaj

(10) Patent No.: US 6,926,871 B1
(45) Date of Patent: Aug. 9, 2005

(54) GAS GENERATION SYSTEM

(75) Inventor: Jyoti Kiron Bhardwaj, Bristol (GB)

(73) Assignee: Surface Technology Systems plc, Newport (GB)

( * ) Notice: Subject to any disclaimer, the term of this patent is extended or adjusted under 35 U.S.C. 154(b) by 0 days.

(21) Appl. No.: 09/674,659

(22) PCT Filed: Mar. 6, 2000

(86) PCT No.: PCT/GB00/00793

§ 371 (c)(1),
(2), (4) Date: Jan. 8, 2001

(87) PCT Pub. No.: WO00/51937

PCT Pub. Date: Sep. 8, 2000

(30) Foreign Application Priority Data

Mar. 4, 1999 (GB) .................................. 9904925
Apr. 29, 1999 (GB) .................................. 9909853

(51) Int. Cl.[7] .............................................. F01N 3/10
(52) U.S. Cl. ........................ 422/174; 422/168; 422/169
(58) Field of Search ............................... 422/174, 168, 422/169, 187, 188, 199, 305, 906

(56) References Cited

U.S. PATENT DOCUMENTS 5,688,384 A * 11/1997 Hodgson et al. ......... 204/228.2
6,079,426 A *  6/2000 Subrahmanyam et al. ... 134/1.1

FOREIGN PATENT DOCUMENTS

| EP | 0150285 A1 | * | 8/1985 | ............ C25B 1/24 |
| JP | 02230720 | * | 9/1990 | ......... H01L 21/205 |
| WO | WO98/27005 | * | 6/1998 | ............ C01B 7/24 |
| WO | WO99/07919 | * | 2/1999 | ............ C25B 1/16 |

* cited by examiner

Primary Examiner—M. Alexandra Elve
(74) Attorney, Agent, or Firm—Volentine Francos & Whitt, PLLC

(57) ABSTRACT

A gas generator system is provided wherein supply sources for halogenated gases, including pure molecular halogens, are connected into a gas reaction chamber, or chamber system, to enable generation of a predetermined gas for localized use in a subsequent process. The reaction chamber has a valved outlet for direct supply of the generated gas to a single or multiple chamber processing tool or process chamber. Thus it is possible, for example, to provide for the localized generation of reactive process gases.

9 Claims, 2 Drawing Sheets

GAS GENERATION SYSTEM

Industrial demands for alternative process gases for dry (plasma and non-plasma) process systems has led to the investigation of a number of different chemistries. Several different highly-reactive halogen-based chemistries are known to be likely candidates to achieve an improved process capability including etch rate, selectivity etc. Gases in this category include pure-halide (inter-halogenated and molecular halogen) compounds and suffer from increased cost (of the delivery and abatement system as well as precursor itself), greater health and safety risks, transportation difficulty (and cost) as well as relatively poor commercial availability.

According to the invention there is provided a gas generator system comprising supply sources for halogenated gases, including pure molecular halogens, connected into a gas reaction chamber or chamber system enabling generation of a predetermined gas for localised use in a subsequent process.

In the preferred arrangement the reaction chamber has a valved outlet for direct supply of the generated gas to a single or multiple chamber processing tool or process chamber.

"Localised" (or point of use) means that the delivery system is located near to a process chamber or a number of chambers or number of systems near to one another, so that the gases created can be delivered directly to the chamber or system for immediate use rather than being created off-site and transported in a suitable container for subsequent introduction into the apparatus.

More than one generator may be used for each process chamber.

In one embodiment, this invention will provide for the localised generation of reactive process gases. These can be generated local to each process tool through the direct combination of different precursor gases under controlled temperature and pressure reaction conditions. Various inter-halogen and compound halogenated gases can be generated in this way. This system can include a feedback system to precisely control the precursor that is being generated.

A second embodiment of this invention will provide for the local on-board synthesis of reactive precursors for plasma and non-plasma processing which include precursors which would otherwise not be readily available due to instability or short-lifetime or difficulty in commercial manufacture or supply. This allows for the direct synthesis and reactive investigation of new groups of halide precursors for semiconductor or non-semiconductor processing.

A third embodiment of this invention provides for the synthesis of precursors that replace directly or indirectly (by simulating the behaviour) the gases that are either in use or have been used in industry and are subject to restriction in use or withdrawal by new environmental legislation. The Montreal Protocol defines environmentally unfriendly chemicals including those that have already been restricted or those that will be restricted in application in the near future. This will impact on the availability of the gases as production is restricted and also on the increasing necessity for abatement during even limited use. Indeed, much recent work has focused on the search for suitable alternative replacement gases (Fracassi and d'Agostino, J. Vac. Sci. Technol. B 16(4), July/August 1998). With suitable abatement means, the synthesis of the material on demand may well be an acceptable means of continuing to use existing chemistries. Commercially this may be the only one of a few solutions available.

The invention further extends to a method of generating gases for localised use in a subsequent process by utilising the system of this invention as defined hereinbefore and using the gas so generated directly in the subsequent process.

The direct combination gas generator can produce a gas in the process chamber by reacting suitable precursor gases possibly with other materials that may be preloaded within a temperature and pressure controlled reaction chamber that is local to a processing tool or chamber. The precursor gases may not react with the substrate being processed, or indeed be desired in the processing tool individually. The design of the system avoids the occurrence in the processing tool or chamber of any possible adverse reactions, during the combination of the precursor gases, that might otherwise prejudice the overall process. Bypass of the process chamber to an abatement tool inhibits the pre-reaction gas mixture from adversely influencing the process in the process chamber. The precursor gases are redirected into the process chamber by the process controller after the required flow and composition has stabilised or wafer loading is complete. The bypass function may also be used during wafer transfer to maintain constant supply quality and conditions.

The precursors for the reaction chamber include any of the following gases:—
1. at least one halogen selected from $F_2$, $Cl_2$, $Br_2$, $I_2$ as the required halogen source;
2. additional gases from $N_2$, $H_2$, $O_2$;
3. additional gases from He, Ar, Kr, Xe.

The generator may further comprise any one or more of the following components:—
1. electrode materials selected from C, B, S, Si, Ge, P in either elemental or appropriate compound form. Where appropriate, the electrode material may be porous to increase the surface reaction area. Metal-containing electrodes may also be used. The electrodes may be independently temperature controlled and electrically and/or magnetically biased;
2. appropriate catalysts (product generation dependent);
3. gas analysers such as infra-red spectroscopes and/or mass spectrometers;
4. a feedback control system which senses the output gas and adjusts reaction parameters (gas flow rates, temperatures, pressure etc) to achieve the desired output concentration;
5. an appropriate reaction vessel or chamber. A number of chambers may be used in series and/or parallel to generate precursors requiring more complex generation mechanisms;
6. an appropriate vacuum control system, valving and gauging, including means for bypassing and purging;
7. an appropriate abatement system.

The generator can operate within the following temperature and pressure range: room temperature to several hundred degrees C. at several Torr to atmospheric pressure. In particular the reaction chamber may be operated at or near atmospheric pressure, going up the range from several Torr to 760 Torr. The reaction chamber temperature can be controlled at between ambient room temperature up to 800° C. generally, but probably will lie within the range of 100–500° C. Differing temperatures may be maintained in at least 2 separate zones of the reaction chamber system. For certain processes, elements of the system may be below room temperature for product purity control. The temperature control of any electrode may be separate from the vessel and the electrode may be independently biassed either electrically and/or magnetically. This or other biassing means may be used to generate a plasma.

The supply to the gas reaction generator of high purity gases removes the need to polish the generated gas to remove unwanted impurities before passing into the process chamber. Mass flow controllers may be used to precisely meter the flow of the supply gases.

The valved control of the flow into the process chamber (if necessary augmented by a control system) ensures that the generator does not experience the low pressure (vacuum) at the process chamber. The preferred method of production of fluorine is by fluoride molten electrolytic generators which can be installed locally to the tool and overcomes the need to obtain high purity 100% fluorine in cylinders. Other means of $F_2$ generation can be appropriately used. The preferred method of supply of $Cl_2$ is from either an electrolytic generator or from high-pressure cylinders, both of which are readily available. Similarly, appropriate sources of $Br_2$, $I_2$ may be used.

Multiple or singular gas inlets and/or either two or more electrodes (or a single composite electrode) as necessary may be used to generate some of the more complex halide species. Electrodes within the reaction chamber may be electrically and/or magnetically biased.

The reaction chamber can be formed from high purity materials (such as those sold under the Trade Marks Monel (nickel/copper/iron alloy), Inconel (nickel/chromium/iron alloy) and Hastalloy (nickel/molybdenum/chromium/manganese/iron alloy)) which would not be financially feasible with large scale generation systems.

The concept of local generation allows the production of the desired process gases to a high purity, although the specific reaction products may be a family of compounds not just one specific product. This can be achieved at a reasonable cost and low risk. The addition of this gas generator, feeding a process tool, allows a novel capability to introduce different generated process gases into the process chamber where, for many different reasons, the option of using the gas directly would not be possible.

The gas generator is able to provide a local supply of various gases on demand, such as:—

1. Inter-halogen compounds including $Cl_xF_y$, $F_xBr_y$, $Cl_xBr_y$ and $F_xCl_yBr_z$ (where $_x$ $_y$ and $_z$ are integers). An $I_2$ source could also be added to provide additional I-containing compound halogens;
2. Groups of halide precursors for plasma and non-plasma processing which include precursors which would otherwise be unavailable due to instability or short-lifetime or difficulty in commercial manufacture or supply;
3. Freons or halo-carbides including $C_xF_y$, $C_wF_xCl_y$, $C_wF_x$-$Br_y$, $C_wF_xCl_yBr_z$, $C_wCl_x$, $C_wCl_xBr_y$, $C_wF_xBr_y$, $C_wBr_y$ (where $_w$, $_x$, $_y$ and $_z$ are integers) An $I_2$ source could also be added to provide additional I-containing halo-carbides;
4. Other reactive halides where the C is replaced by N or B;
5. Other reactive halides where any C is replaced by combination of C with N, B and/or H;
6. Metal halides, where the C source is replaced by an appropriate metal-containing electrode, (including W, Mo, Ti and Ta);
7. Halide complexes of any combination of the groups listed in 3, 4, 5 and 6 above.

Ideal gases for generation include ClF, $ClF_3$, $ClF_5$, $BrF_3$, $WF_6$, $MoF_6$, $TiF_4$, $TiCl_4$, $TaF_5$, BrF, $CF_4$, $C_2F_6$, $C_3F_8$, $CHF_3$, $CF_2H_2$, $CCl_2F_2$, $CCl_4$, $CF_3Br$ and $NF_3$, and related compounds. An appropriate selection of precursors can also be used to synthesise or generate organo-metallic compounds.

The generator of the invention offers many advantages over direct gas delivery. For some of the gases the reaction gas generator can operate at or near atmospheric pressure, thereby eliminating the need for high-pressure regulators on the system. Installation and storage of hazardous gases is reduced. The local generation, on demand, of the hazardous gases eliminates long (and usually high-pressure) gas lines from a central store to the installation and minimises associated safety risks. There would be a significant reduction in the installation costs due to the reduced level of plumbing of additional gases and the associated safety requirements. The maintenance of the complete system is eased by the absence of any of the generated gases when the system is not operating. The quantity of the generated gases can be regulated to that required for the specific application so that the gas consumption is optimised and excess generated gas avoided. Some gases may require higher generation pressures (above atmospheric) and hence necessitate the use of pressure regulatory devices.

The invention may be performed in various ways and preferred embodiments thereof will now be described, by way of example, with reference to the accompanying drawings, in which:—

FIG. 1 is a diagrammatic illustration of a general gas generation system of this invention;

FIG. 2 indicates various input and control features of the system of FIG. 1;

Figure 1:
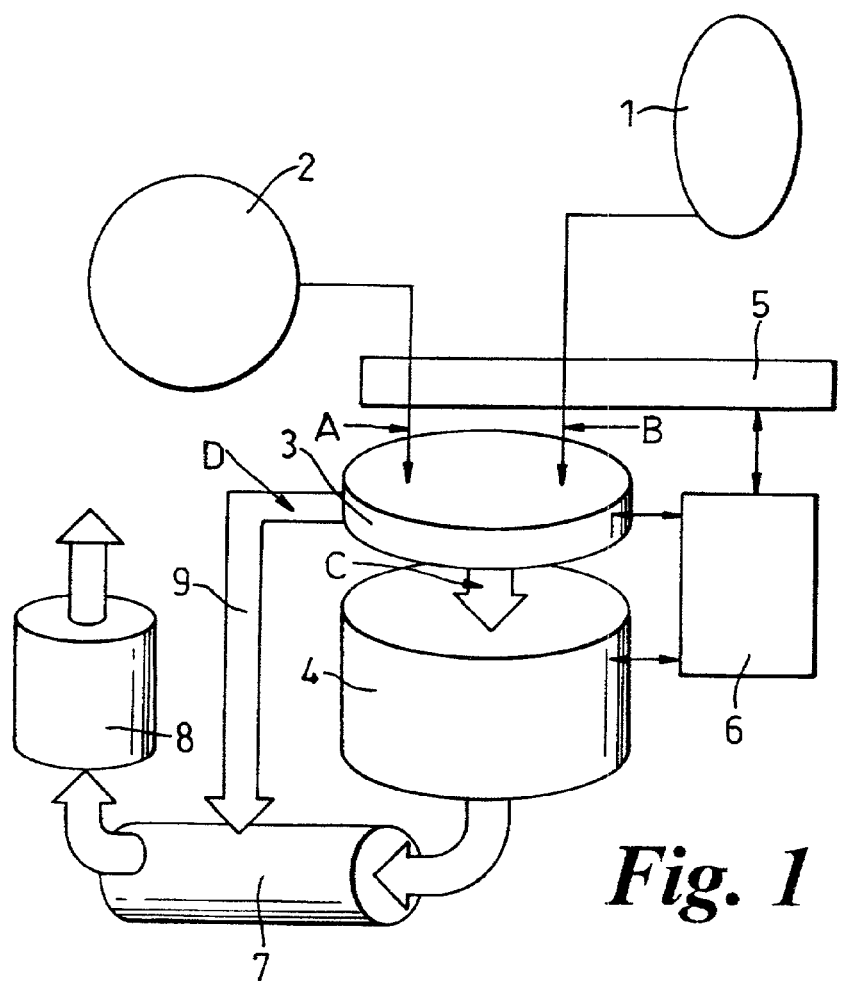

In the arrangement shown in FIG. 1 precursor gases are passed from suitable supply sources 1 and 2 to a reaction chamber 3 where the gases are combined under controlled conditions. The reaction product is then fed to a process chamber 4 where a dry process utilising that gas is to take place. Appropriate valving will include valves provided at A, B, C and D for appropriate control and isolation means. Linked control systems 5 and 6 monitor and maintain the supply to and the conditions in the chambers 3 and 4.

From the process chamber 4 gases pass to an exhaust system 7, which in turn leads to an abatement tool 8 (which is usually needed). A bypass outlet 9 leads from the reaction chamber 3 to the exhaust system, whereby gases can be switched into the process chamber only when required for processing. This also allows the means for ensuring stable gas composition and flow to be maintained prior to switching into the process chamber.

Figure 2:
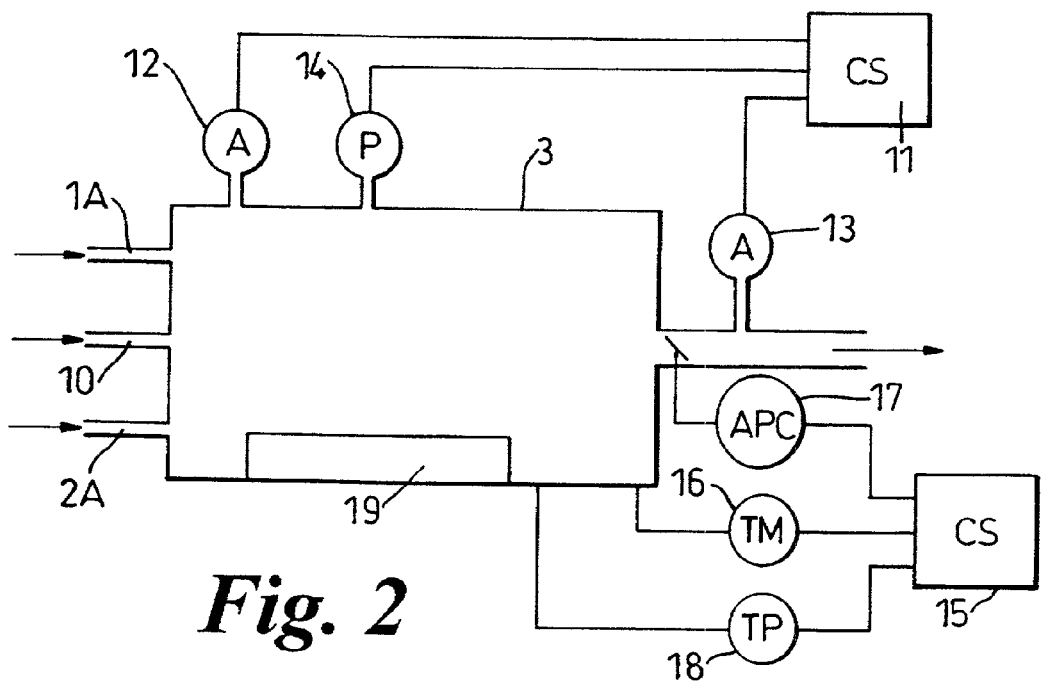

FIG. 2 shows features of the reaction chamber 3, and connections thereto, in greater detail. This illustrates inlets 1A and 2A from sources 1 and 2 and another inlet 10 for a third precursor gas (there could be still further inlets if required). A control system 11 (which is a single system but for clarity is shown in two parts 11 and 15) can take measurements from analysis devices 12 and 13 and a pressure-measuring device 14. The control system 15 can take measurements from a temperature measurement device 16 and also provide control for an auto pressure control device 17 and a temperature control device 18. Optionally an electrode 19 can be provided within the reaction chamber 3 with biassing means (not shown) and a temperature control device (not shown).

Figure 3:
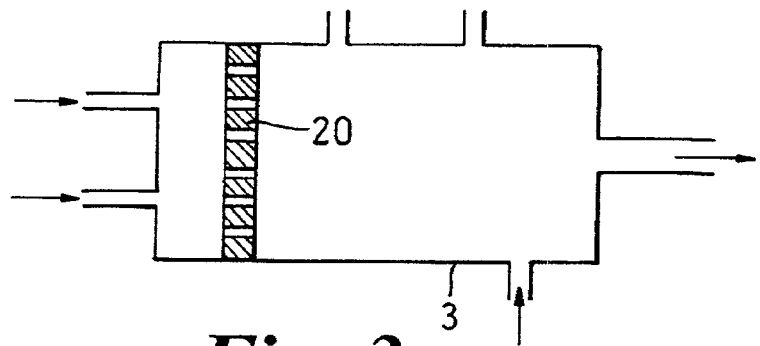
FIG. 3 shows a modified system for that indicated in FIG. 2.
Figure 4:
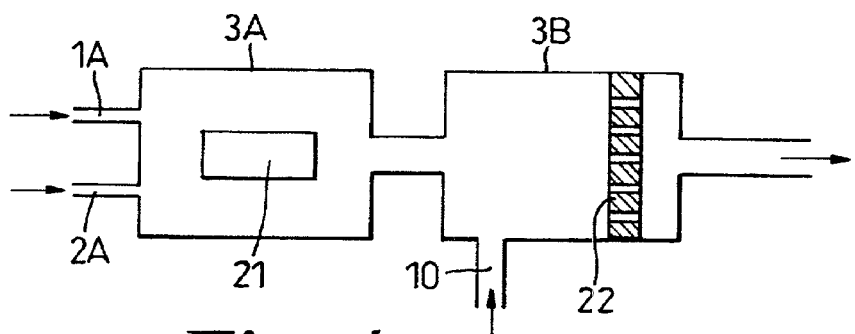
FIGS. 4, 5 and 6 illustrate still further modifications of the general gas generation system illustrated in FIG. 1.
Figure 5:
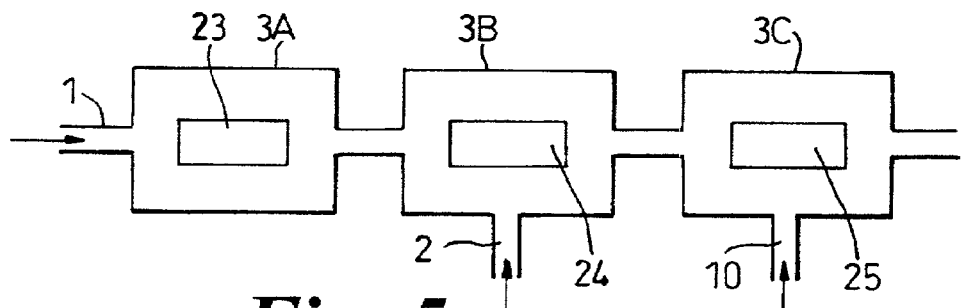
Figure 6:
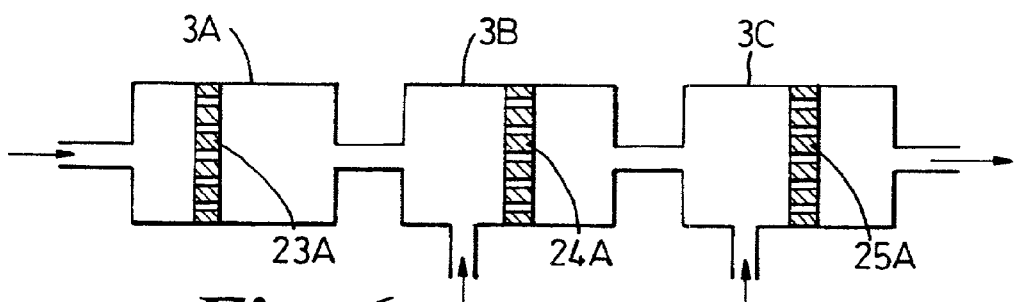

FIGS. 3, 4, 5 and 6 illustrate various ways in which electrodes can be incorporated into the reaction chamber 3 (which in turn may comprise a single chamber or a combination of chambers linked in serial or parallel or any desired combination thereof). In FIG. 3 the chamber 3 is shown as being provided with a porous electrode 20. FIG. 4 illustrates a two chamber system wherein the preliminary reaction chamber 3A incorporates a normal electrode 21 whilst a downstream chamber 3B incorporates a porous electrode 22. The third gas supply line 10 is connected to this secondary chamber 3B. In FIG. 5 three linked reaction chambers 3A, 3B and 3C are shown, each incorporating a standard electrode 23, 24 and 25 with respective gas supply sources 3, 4 and 10. In the modified arrangement shown in FIG. 6 the chambers 3A, 3B and 3C are modified to incorporate porous electrodes 23A, 24A and 25A.

The procedures of this invention are particularly useful additionally as a method of local creation of a number of short shelf-life organo-metallic compounds using suitable precursors.

What is claimed is:

1. A method of generating a reactive process gas to be used in a subsequent process, the method comprising:
   providing gas supply sources which are connected to a gas reaction chamber or chamber system, at least one of said gas supply sources providing a pure molecular halogen gas which is fed directly into the reaction chamber, and
   introducing gases from said sources into the reaction chamber/chamber system under conditions wherein the gases react to form the reactive process gas which is collected in said reaction chamber/system prior to being fed to the subsequent process.

2. A method according to claim 1, wherein the subsequent process is carried out in a process chamber or a single or multiple chamber processing tool or tools that are supplied with the reactive process gas via an outlet from said gas reaction chamber or chamber system.

3. A method according to claim 1 further comprising providing for the localized generation of a reactive process gas.

4. A method according to claim 1 further comprising providing for the local synthesis of reactive precursors for plasma or non-plasma processing.

5. A gas generator system adapted to be used in a method of claim 1, wherein the gas generator system comprises a gas reaction chamber or chamber system having gas inlets so that precursor gas from gas supply sources can be directly introduced into said chamber/chamber system, wherein at least one of the supply sources incorporates a pure molecular halogen gas generator, and wherein the gas reaction chamber or chamber system includes an outlet from which the reactive gas generated in said chamber/chamber system is supplied directly to a process chamber for a subsequent reaction whilst the reactive gas is being generated.

6. A gas generator system according to claim 5, wherein the outlet includes a valve to control flow of the reactive gas to the subsequent reaction being carried out in the process chamber.

7. A gas generator system according to claim 5, including control systems with reactive and process chambers, wherein properties of the reactive gas are analyzed either in chamber or as it flows to chamber and, based on the results, reaction parameters in the gas reaction chamber or chamber system are adjusted to achieve predetermined parameters for the reactive gas and/or to control flow to the process chamber.

8. A gas generator system according to claim 5, wherein the reactive chamber includes one or more electrodes for production of a plasma when precursors reach the chamber.

9. A gas generator system according to claim 5, wherein the reaction chamber includes a bypass outlet through which a gas produced in said chamber is selectively caused to bypass the process chamber.

\* \* \* \* \*